(12) United States Patent
Podolski et al.

(10) Patent No.: US 7,173,064 B2
(45) Date of Patent: Feb. 6, 2007

(54) METHODS AND COMPOSITIONS WITH TRANS-CLOMIPHENE FOR TREATING WASTING AND LIPODYSTROPHY

(75) Inventors: Joseph S. Podolski, The Woodlands, TX (US); Ronald Wiehle, Houston, TX (US)

(73) Assignee: Repros Therapeutics Inc., The Woodlands, TX (US)

( * ) Notice: Subject to any disclaimer, the term of this patent is extended or adjusted under 35 U.S.C. 154(b) by 212 days.

(21) Appl. No.: 10/712,546

(22) Filed: Nov. 12, 2003

(65) Prior Publication Data

US 2004/0171697 A1    Sep. 2, 2004

Related U.S. Application Data

(63) Continuation-in-part of application No. 10/427,768, filed on Apr. 30, 2003, which is a continuation-in-part of application No. PCT/US02/021524, filed on Jul. 9, 2002.

(60) Provisional application No. 60/304,313, filed on Jul. 9, 2001.

(51) Int. Cl.
*A61K 31/137* (2006.01)

(52) U.S. Cl. .................................................. 514/651

(58) Field of Classification Search ................ 514/651
See application file for complete search history.

(56) References Cited

U.S. PATENT DOCUMENTS

| 4,061,733 | A | 12/1977 | Gunjikar |
|---|---|---|---|
| 5,728,688 | A | 3/1998 | Labrie |
| 5,861,389 | A | 1/1999 | Radlmaier |
| 6,096,338 | A | 8/2000 | Lacy |
| 6,126,969 | A | 10/2000 | Shah |
| 6,129,933 | A | 10/2000 | Oshlack |
| 6,143,353 | A | 11/2000 | Oshlack |
| 6,190,591 | B1 | 2/2001 | Van Lengerich |
| 6,221,399 | B1 | 4/2001 | Rolfes |
| 6,248,363 | B1 | 6/2001 | Patel |
| 6,391,920 | B1 | 5/2002 | Fisch |
| 6,583,129 | B1 * | 6/2003 | Mazer et al. ............ 514/167 |
| 6,743,448 | B2 * | 6/2004 | Kryger ...................... 424/489 |
| 2002/0120012 | A1 | 8/2002 | Fisch |
| 2004/0220154 | A1 * | 11/2004 | Kryger ...................... 514/171 |

FOREIGN PATENT DOCUMENTS

| EP | 0888775 A2 | 7/1999 |
|---|---|---|
| JP | 4-312522 | 11/1992 |
| WO | WO 95/35093 | 12/1995 |
| WO | WO 01/91744 A1 | 12/2001 |
| WO | WO 03/005954 A2 | 1/2003 |

OTHER PUBLICATIONS

Tenover, J., et al., "The Effects of Aging in Normal Men on Bioavailable Testosterone and Luteinizing Hormone Secretion: Response to Clomiphene Citrate," Journal Clinical Endocrinol. Metab., vol. 65, No. 6, pp. 1118-1126 (1987).

Chang, C-F, et al., "Stimulation of Ovulation in Ayu, *Plecoglossus-Altivelis*, by Treatment with Antiestrogens and Luteinizing Hormone-Releasing Hormone Analog," Aquaculture, vol. 101, Nos. 3-4, pp. 329-336 (1992).

* cited by examiner

*Primary Examiner*—Brian Kwon
(74) *Attorney, Agent, or Firm*—Howrey LLP

(57) ABSTRACT

The present invention discloses compositions and methods useful for treating wasting, especially a loss of muscle mass. The present invention also discloses compositions and methods useful for treating lipodystrophy. The compositions and methods of the present invention are particularly beneficial to HIV-infected individuals.

7 Claims, 3 Drawing Sheets

Normal Secretory Total Serum Testosterone Profiles in Healthy Young and Older Men

METHODS AND COMPOSITIONS WITH TRANS-CLOMIPHENE FOR TREATING WASTING AND LIPODYSTROPHY

CROSS-REFERENCES TO RELATED APPLICATIONS

This application is a continuation-in-part of U.S. application Ser. No. 10/427,768, filed as Apr. 30, 2003, which is a continuation-in-part of International Application No. PCT/US02/021524, filed Jul. 9, 2002, which claims the benefit, under 35 U.S.C. §119(e), of U.S. Provisional Patent Application No. 60/304,313, filed on Jul. 9, 2001. This application is also a continuation-in-part of International Application No. PCT/US02/021524, filed Jul. 9, 2002. The contents of all applications are incorporated herein by reference in their entirety.

BACKGROUND

1. Field of the Invention

The present invention relates to treatments for increasing muscle mass. More specifically, the present invention relates to treatments for wasting and lipodystrophy including, but not limited to, in HIV-infected individuals. The present invention also relates to treatments for increasing CD4$^+$ lymphocyte levels, particularly in HIV-infected individuals.

2. Description of Related Art a. HIV

Infection with the HIV virus and the subsequent disease known as AIDS manifests itself clinically in a loss of CD4$^+$ T lymphocytes that are targets of the virus. HIV-positive patients monitor their disease through periodic assessment of CD4$^+$ lymphocyte counts or the CD4$^+$/CD8$^+$ lymphocyte ratio and use these measurements for making a decision when to begin AIDS therapies or how to tailor the therapies. Men with AIDS often face not only the wasting and debilitating effects of opportunistic microbiological infections typical of AIDS, but also a loss of muscle mass as part of a condition known as lipodystrophy. In addition to muscle mass loss, lipodystrophy is characterized by a build-up of fat in certain body areas, a loss of fat in certain body areas, high levels of triglycerides and cholesterol in the blood, and high levels of blood glucose and insulin. The condition is aggravated or may be caused directly by drug cocktails used to treat AIDS. Current treatments for symptoms associated with lipodystrophy include plastic surgery such as liposuction, diet and exercises, lipid-lowering drugs and anabolic drugs.

Men and women present lipodystrophy differently, consequently, sex hormones may play a role in onset of the disease. In support of this observation, many HIV-positive men experience significant endocrine problems such as decreased production of IGF and testosterone. Hypogonadism is a common problem in HIV-infected men with rates from 25% to 45%, depending on the stage of AIDS disease. Possible causes of hypogonadism include infections of the testicles (including with HIV), drug side effects (including side effects from ketoconazole, ganciclovir, and megestrol acetate) and elevated cortisol.

b. Testosterone Therapy

Testosterone therapy is being used in up to 80% of the HIV-infected men with a loss of muscle mass. Testosterone is the primary male androgen, playing a vital role in overall male health. Testosterone is essential to the development and maintenance of specific reproductive tissues (testes, prostate, epididymis, seminal vesicle, and penis) and male secondary sex characteristics. It plays a key role in libido and erectile function and is necessary for the initiation and maintenance of spermatogenesis. Testosterone also has important functions not related to reproductive tissues. For example, it positively affects body composition by increasing nitrogen retention, which supports lean body mass, muscle size and strength. It also acts on bone to stimulate bone formation.

Testosterone deficiency can result from disease or genetic disorders and is also frequently a complication of aging. Some of the sequelae of adult testosterone deficiency include a wide variety of symptoms including: loss of libido, erectile dysfunction, oligospermia or azoospermia, absence or regression of secondary sexual characteristics, progressive decrease in muscle mass, fatigue, depressed mood and increased risk of osteoporosis.

Several forms of testosterone therapy exist in the United States today. Recently, transdermal preparations have gained favor in the market. However, a scrotal testosterone patch results in supraphysiologic levels of 5α-dihydrotestosterone (DHT) due to the high concentration of 5α-reductase in scrotal skin. It is not known whether these elevated DHT levels have any long-term health consequences. Nonscrotal systems are considered more convenient and most patients achieve average serum concentrations within the normal range and have normal levels of DHT. Oral testosterone therapy is not recommended because doses required for replacement therapy are associated with significant risk of hepatotoxicity.

Testosterone therapy is beneficial in HIV-infected men with a loss of muscle mass. Testosterone therapy has positive effects on the fat-free muscle mass, bone, memory, libido and sense of well-being in HIV-infected men. However, high amounts of testosterone increase the risk of cardiovascular disease and benign prostate hyperplasia (BPH). Although testosterone therapy is able to inhibit wasting in HIV-infected men, it has not been shown to beneficially alter CD4$^+$ levels or viral load.

c. Clomiphene

Clomiphene, which is an antiestrogen related to tamoxifen, has also been used to treat men with low testosterone levels. Clomiphene blocks the normal estrogen feedback on the hypothalamus and subsequent negative feedback on the pituitary. This leads to increases in luteinizing hormone (LH) and follicle stimulating hormone (FSH). In men, these increased levels of gonadotropins stimulate the Leydig cells of the testes and result in the production of higher testosterone levels.

Tenover et al., J. Clin. Endocrinol. Metab. 64:1103, (1987) and Tenover et al., J. Clin. Endocrinol. Metab. 64:1118 (1987) found increased in FSH, LH in both young and old men after treatment with clomiphene. They also found increases in free and total testosterone in men with young men showing significant increases.

Studies were also conducted to determine whether or not clomiphene could be used to improve fertility in men by improving semen quality. Homonnai et al. Fertil. and Steril 50:801 (1988) saw increases in sperm concentration and count but others have not. (See e.g., Sokel, et al., Fertil. and Steril. 49:865 (1988); Check, et al., Int. J. Fertil. 34:120 (1989); Purvis, et al., Int. J. Androl 21:109 (1989); and Breznik, Arch. Androl. 21:109 (1993).) One group saw a deterioration in the percentage of normal sperm with long-term treatment. Shamis, et al., Arch. Androl 21:109 (1991). A WHO study showed no changes in semen quality or fertility after 6 months of treatment. (Androl. 15:299 (1992).) A meta-analysis seems to confirm that testosterone levels go up in men with poor quality sperm but not fertility. (Vanderkerckhove, et al., 2000).

Vandekerckhove, et al. (Cochrane Database Syst Rev 2000;(2):CD000151 (2000)) noted that ten studies involving 738 men have suggested that anti-estrogens appear to have a beneficial effect on endocrinal outcomes, i.e. testosterone, but there is not enough evidence to evaluate fertility effects. Nevertheless should clomiphene administration enhance testosterone levels then one could easily conclude that the drug should positively impact the side effects of testosterone deprivation as long as the testes still retain the ability to respond to gonadotropin stimulation.

Ernst et al., J. Pharmaceut. Sci. 65:148 (1976), have shown that clomiphene is a mixture of two geometric isomers which they refer to as cis,-Z-, clomiphene (cis-clomiphene or zuclomiphene) and trans-,E-, clomiphene, (trans-clomiphene or enclomiphene). According to Ernst, et al. Trans-clomiphene HCl has a melting point of 149° C.–150.5° C., while cis-clomiphene HCl has a melting point of 156.5° C.–158° C. Ernst et al. have also noted that (the trans-isomer) is antiestrogenic (AE) while the cis-isomer is the more potent and more estrogenic form and has also been reported to have anti-estrogenic activity. The authors attribute the effect of the drug on ovulatory activity to both forms stating that the mixture is more effective than trans-clomiphene alone. The trans-isomer aids ovulation at the level of the hypothalamus. The estrogenic isomer cis-clomiphene contributes to enhanced ovulation elsewhere in the physiologic pathway leading to ovulation. The isomers are also reported to have different in vivo half-life. Furthermore the cis form has been reported to leave residual blood levels for in excess of one month following a single dose.

Clomiphene is currently approved as a mixture of both cis- and trans-isomers, the cis-isomer being present as about 30% to 50% (Merck Manual) for fertility enhancement in the anovulatory patient. Clomiphene improves ovulation by initiating a series of endocrine events culminating in a preovulatory gonadotropin surge and subsequent follicular rupture. The drug is recommended to be administered for 5 days at a dose of up to 100 mg daily. Clomiphene has also been associated with numerous side effects including: blurred vision, abdominal discomfort, gynecomastia, testicular tumors, vasomotor flushes, nausea, and headaches. Furthermore, other studies suggest that clomiphene possesses both genotoxic and tumor enhancement effects. The net outcome of these observations is that clomiphene in its current format, having between 30% and 50% of the cis isomer, would be unacceptable for chronic therapy in men.

There continues to be a need for methods of treating wasting in HIV-infected patients. The present invention addresses this need and provides novel compositions and methods for treating wasting in HIV-infected patients.

SUMMARY

The present invention relates to a composition comprising 0% to about 29% w/w of cis-clomiphene and about 100% to about 71% trans-clomiphene or analogs thereof or pharmaceutically acceptable salts or solvates thereof. The composition may further comprise one or more pharmaceutically acceptable diluents, adjuvants, carriers or excipients.

The present invention also relates to a composition comprising cis-clomiphene and trans-clomiphene or analogs thereof or pharmaceutically acceptable salts or solvates thereof, wherein the ratio of trans-clomiphene and cis-clomiphene is greater than 71/29. The composition may further comprise one or more pharmaceutically acceptable diluents, adjuvants, carriers or excipients.

The present invention also relates to a composition consisting essentially of trans-clomiphene or analogs thereof or pharmaceutically acceptable salts or solvates thereof. The composition may further comprise one or more pharmaceutically acceptable diluents, adjuvants, carriers or excipients.

The present invention also relates to a method for treating wasting in a mammal, comprising administering to the mammal an effective amount of a composition comprising 0% to about 29% w/w of cis-clomiphene and about 100% to about 71% trans-clomiphene or analogs thereof or pharmaceutically acceptable salts or solvates thereof. The composition may further comprise one or more pharmaceutically acceptable diluents, adjuvants, carriers or excipients. The mammal may be a male or a female. The mammal may also be a human. The human may be infected with HIV.

The present invention also relates to a method for treating wasting in a mammal, comprising administering to the mammal an effective amount of a composition comprising cis-clomiphene and trans-clomiphene or analogs thereof or pharmaceutically acceptable salts or solvates thereof, wherein the ratio of trans-clomiphene and cis-clomiphene is greater than 71/29. The composition may further comprise one or more pharmaceutically acceptable diluents, adjuvants, carriers or excipients. The mammal may be a male or a female. The mammal may also be a human. The human may be infected with HIV.

The present invention also relates to a method for treating wasting in a mammal, comprising administering to the mammal an effective amount of a composition consisting essentially of trans-clomiphene or analogs thereof or pharmaceutically acceptable salts or solvates thereof. The composition may further comprise one or more pharmaceutically acceptable diluents, adjuvants, carriers or excipients. The mammal may be a male or a female. The mammal may also be a human. The human may be infected with HIV.

The present invention also relates to a method for modulating muscle mass in a mammal, comprising administering to the mammal an effective amount of a composition comprising 0% to about 29% w/w of cis-clomiphene and about 100% to about 71% trans-clomiphene or analogs thereof or pharmaceutically acceptable salts or solvates thereof. The composition may further comprise one or more pharmaceutically acceptable diluents, adjuvants, carriers or excipients. The mammal may be a male or a female. The mammal may also be a human. The human may be infected with HIV.

The present invention also relates to a method for modulating muscle mass in a mammal, comprising administering to the mammal an effective amount of a composition comprising cis-clomiphene and trans-clomiphene or analogs thereof or pharmaceutically acceptable salts or solvates thereof, wherein the ratio of trans-clomiphene and cis-clomiphene is greater than 71/29. The composition may further comprise one or more pharmaceutically acceptable diluents, adjuvants, carriers or excipients. The mammal may be a male or a female. The mammal may also be a human. The human may be infected with HIV.

The present invention also relates to a method for modulating muscle mass in a mammal, comprising administering to the mammal an effective amount of a composition consisting essentially of trans-clomiphene or analogs thereof or pharmaceutically acceptable salts or solvates thereof. The composition may further comprise one or more pharmaceutically acceptable diluents, adjuvants, carriers or excipients. The mammal may be a male or a female. The mammal may also be a human. The human may be infected with HIV.

The present invention also relates to a method for modulating cholesterol levels in a mammal, comprising administering to the mammal an effective amount of a composition comprising 0% to about 29% w/w of cis-clomiphene and about 100% to about 71% trans-clomiphene or analogs thereof or pharmaceutically acceptable salts or solvates thereof. The composition may further comprise one or more pharmaceutically acceptable diluents, adjuvants, carriers or excipients. The mammal may be a male or a female. The mammal may also be a human. The human may be infected with HIV.

The present invention also relates to a method for modulating cholesterol levels in a mammal, comprising administering to the mammal an effective amount of a composition comprising cis-clomiphene and trans-clomiphene or analogs thereof or pharmaceutically acceptable salts or solvates thereof, wherein the ratio of trans-clomiphene and cis-clomiphene is greater than 71/29. The composition may further comprise one or more pharmaceutically acceptable diluents, adjuvants, carriers or excipients. The mammal may be a male or a female. The mammal may also be a human. The human may be infected with HIV.

The present invention also relates to a method for modulating cholesterol levels in a mammal, comprising administering to the mammal an effective amount of a composition consisting essentially of trans-clomiphene or analogs thereof or pharmaceutically acceptable salts or solvates thereof. The composition may further comprise one or more pharmaceutically acceptable diluents, adjuvants, carriers or excipients. The mammal may be a male or a female. The mammal may also be a human. The human may be infected with HIV.

The present invention also relates to a method for treating lipodystrophy in a mammal, comprising administering to the mammal an effective amount of a composition comprising 0% to about 29% w/w of cis-clomiphene and about 100% to about 71% trans-clomiphene or analogs thereof or pharmaceutically acceptable salts or solvates thereof. The composition may further comprise one or more pharmaceutically acceptable diluents, adjuvants, carriers or excipients. The mammal may be a male or a female. The mammal may also be a human. The human may be infected with HIV.

The present invention also relates to a method for treating lipodystrophy in a mammal, comprising administering to the mammal an effective amount of a composition comprising cis-clomiphene and trans-clomiphene or analogs thereof or pharmaceutically acceptable salts or solvates thereof, wherein the ratio of trans-clomiphene and cis-clomiphene is greater than 71/29. The composition may further comprise one or more pharmaceutically acceptable diluents, adjuvants, carriers or excipients. The mammal may be a male or a female. The mammal may also be a human. The human may be infected with HIV.

The present invention also relates to a method for treating lipodystrophy in a mammal, comprising administering to the mammal an effective amount of a composition consisting essentially of trans-clomiphene or analogs thereof or pharmaceutically acceptable salts or solvates thereof. The composition may further comprise one or more pharmaceutically acceptable diluents, adjuvants, carriers or excipients. The mammal may be a male or a female. The mammal may also be a human. The human may be infected with HIV.

The present invention also relates to a method for modulating lymphocyte levels in a mammal, comprising administering to the mammal an effective amount of a composition comprising 0% to about 29% w/w of cis-clomiphene and about 100% to about 71% trans-clomiphene or analogs thereof or pharmaceutically acceptable salts or solvates thereof. The lymphocyte levels modulated may be $CD4^+$ T lymphocyte levels. The composition may further comprise one or more pharmaceutically acceptable diluents, adjuvants, carriers or excipients. The mammal may be a male or a female. The mammal may also be a human. The human may be infected with HIV.

The present invention also relates to a method for modulating lymphocyte levels in a mammal, comprising administering to the mammal an effective amount of a composition comprising cis-clomiphene and trans-clomiphene or analogs thereof or pharmaceutically acceptable salts or solvates thereof, wherein the ratio of trans-clomiphene and cis-clomiphene is greater than 71/29. The lymphocyte levels modulated may be $CD4^+$ T lymphocyte levels. The composition may further comprise one or more pharmaceutically acceptable diluents, adjuvants, carriers or excipients. The mammal may be a male or a female. The mammal may also be a human. The human may be infected with HIV.

The present invention also relates to a method for modulating lymphocyte levels in a mammal, comprising administering to the mammal an effective amount of a composition consisting essentially of trans-clomiphene or analogs thereof or pharmaceutically acceptable salts or solvates thereof. The lymphocyte levels modulated may be $CD4^+$ T lymphocyte levels. The composition may further comprise one or more pharmaceutically acceptable diluents, adjuvants, carriers or excipients. The mammal may be a male or a female. The mammal may also be a human. The human may be infected with HIV.

DETAILED DESCRIPTION

Figure 1:
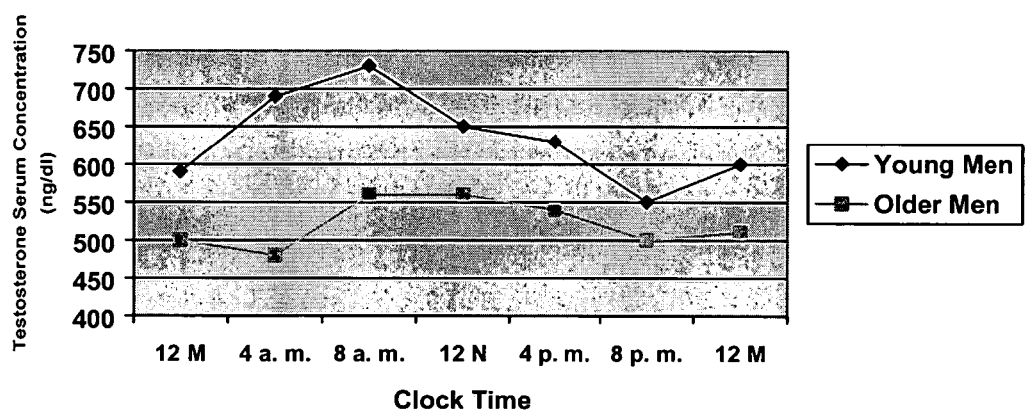
FIG. 1 is a graphic representative of the normal secretory total serum testosterone profiles in healthy men (young and old).
Figure 2:
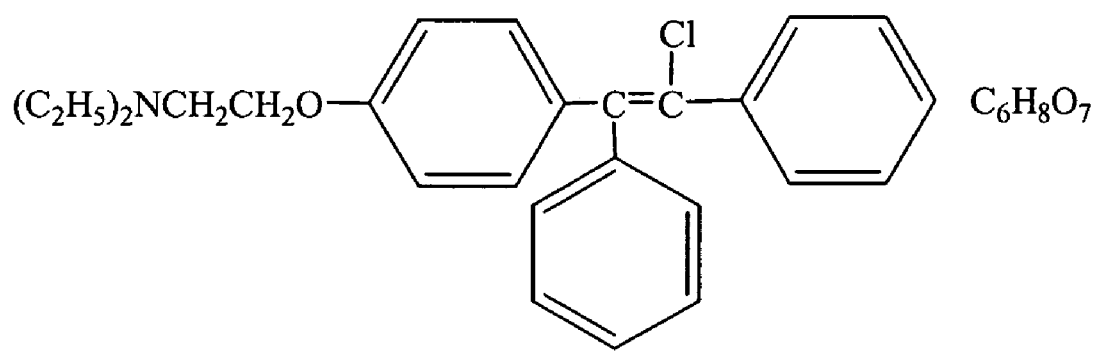
FIG. 2 shows the chemical structure of clomiphene citrate.

The present invention is directed to compositions comprising clomiphene with increased amounts of trans-clomiphene. The trans-isomer of clomiphene is an anti-estrogen, whereas the cis-isomer of clomiphene is estrogenic. By increasing the relative amount of the trans-isomer in clomiphene-containing compositions, the antiestrogenic properties of the trans-isomer may be taken advantage of while lowering or eliminating potential side effects caused by the estrogenic cis-isomer.

In one aspect of the present invention, the composition comprises 0% to about 29% w/w of cis-clomiphene and about 100% to about 71% trans-clomiphene or analogs thereof or pharmaceutically acceptable salts or solvates thereof. In another aspect of the present invention, the composition comprises cis-clomiphene and trans-clomiphene or analogs thereof or pharmaceutically acceptable salts or solvates thereof, wherein the ratio of trans-clomiphene and cis-clomiphene is greater than 71/29. In yet another aspect of the present invention, the composition consists essentially of trans-clomiphene or analogs thereof or pharmaceutically acceptable salts or solvates thereof. The compositions of the present invention may further comprise one or more pharmaceutically acceptable diluents, adjuvants, carriers or excipients.

The compositions of the present invention may be administered to a mammal in order to obtain beneficial effects of an antiestrogen including, but not limited to, increased levels of testosterone. The compositions of the present invention may be administered to a mammal for increasing or modulating muscle mass, bone density, libido, potency, body performance capacity, memory, lymphocyte levels and in particular CD4+ T lymphocyte levels. The compositions of the present invention may also be administered to a mammal for decreasing or modulating cholesterol levels, depression, anxiety, irritability, and insomnia. The compositions of the present invention may also be administered to a mammal for treating wasting and lipodystrophy.

The compositions of the present invention may be administered to any mammal that would benefit from increased levels of testosterone. The mammal may be a male or a female. The mammal may be a human.

The compositions of the present invention may also be administered to a person infected with HIV. In order to prevent wasting and a loss of muscle mass, HIV-infected individuals are often treated with agents that raise testosterone levels. Compositions comprising trans-clomiphene may be used in HIV-infected patients as an alternative to testosterone therapy. Trans-clomiphene treatment has low liver and kidney toxicity and favorable effects on cholesterol, lipids and lymphocyte levels, which is especially beneficial for HIV-infected individuals. Moreover, treatment with trans-clomiphene may have reduced side effects compared to testosterone therapy, such as PSA and cardiovascular risks.

Compositions comprising trans-clomiphene may also increase In terms of cost, increasing CD4+ lymphocytes could delay AIDS onset and delay the start of therapy:

The terms "treat" or "treatment", as used in the instant application, refer to both therapeutic treatment and prophylactic or preventative measures, wherein the object is to prevent or slow down (lessen) an undesired physiological change or disorder, such as symptoms associated with AIDS or the treatment thereof. For purposes of the present invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Individuals in need of treatment include those already with the condition or disorder as well as those prone to develop the condition or disorder or those in whom the condition or disorder is to be prevented.

The terms "modulate" or "modulating", as used in the instant application, refer to both therapeutic treatment and prophylactic or preventative measures, wherein the object is to prevent or slow down (lessen) an undesired clinical parameter, such as muscle mass, cholesterol levels, lymphocyte levels, or CD4+ T lymphocyte levels. For purposes of the present invention, beneficial or desired clinical results include, but are not limited to, correcting of clinical parameter, diminishment of extent of clinical parameter, stabilized (i.e., not worsening) clinical parameter, and delay or slowing of extent of clinical parameter.

Suitable pharmaceutical compositions or unit dosage form may be in the form of solids, such as tablets or filled capsules or liquids such as solutions suspensions, emulsions, elixirs or capsules filled with the same, all for oral use. The compositions may also be in the form of sterile injectable solutions or emulsions for parenteral (including subcutaneous) use. Such pharmaceutical compositions and unit dosage forms thereof may comprise ingredients in conventional proportions.

Compositions according to the present invention may be administered by any route of administration including, but not limited to, intravenous, subcutaneous, buccal, transmucosal, intrathecal, intradermal, and intracisternal.

Compositions according to the present invention may comprise trans-clomiphene at a dosage between one mg to about 200 mg (although the determination of optimal dosages is within the level of ordinary skill in the art). The composition may comprise trans-clomiphene at a dosage of about 1 mg, 2 mg, 3 mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg 180 mg, 190 mg, 200 mg, or there between. The composition may comprise trans-clomiphene and cis-clomiphene at a ratio of about 71/29, 72/28, 73/27, 74/26, 75/25, 76/24, 77/23, 78/22, 79/21, 80/20, 81/19, 82/18, 83/17, 84/16, 85/15, 86/14, 87/13, 88/12, 89/11, 90/10, 91/9, 92/8, 93/7, 94/6, 95/5, 96/4, 97/3, 98/2, 99/1, 99.5/0.5, or there between. Analogs of the trans-and cis-isomers of clomiphene such as those described in Ernst, et al. supra are also useful in the practice of the present invention.

Dosages are preferably (but not necessarily) administered as part of a dosage regimen designed to give rise to serum testosterone levels that mimic or correspond to the normal secretary total serum testosterone profile described in FIG. 1. For example, according to FIG. 1 a dosage of the preferred composition may be administered in a pharmaceutical formulation that would give rise to peak serum testosterone levels at around 8 a.m. Such pharmaceutical formulations may be in the form of sustained release formulations prepared as described for example in U.S. Pat. No. 6,221,399, Japanese patent 4-312522, Meshali et al, Int. J. Phar. 89:177–181 (1993), Kharenko et al, Intern. Symp. Control Rel. Bioact. Mater. 22:232–233 (1995), WO 95/35093, Dangprasit et al., Drug. Devel. and Incl. Pharm. 21 (20): 2323–2337 (1995); U.S. Pat. Nos. 6,143,353, 6,190,591, 6,096,338, 6,129,933, 6,126,969, 6,248,363 and other sustained release formulations well known in the art.

In another embodiment of the present invention, one or more dosages of an effective amount of composition comprising trans-clomiphene at a dosage between one mg to about 200 mg are administered to a patient who has a need to decrease his serum cholesterol levels. The patient may be a male or a female. Cis-clomiphene may also be present in the composition as long as the ratio of trans-clomiphene to cis-clomiphene is greater than 1. Analogs of the trans-and cis-isomers of clomiphene such as those described in Ernst, et al. supra are also useful in the practice of the present invention.

All of the references discussed herein are incorporated by reference in their entirety.

The following Examples are meant to be illustrative of the invention and are not intended to limit the scope of the invention as set out in the appended claims.

EXAMPLE 1

Effects of Clomids on Serum Testosterone and Cholesterol in Male Baboons

Adult, male Baboons were given 1.5 mg/kg of Clomid, Trans-clomiphene (trans-Clomid) or Zuclomid (cis-Clomid)

for 12 consecutive days. The samples analyzed were sera taken on the day of first treatment before being given test article (day 0), after 12 days of treatment (day 12) and 7 days after the last treatment (end or wash-out).

1. Effects on Body Weight and Serum LH, FSH, PRL and Testosterone

Figure 3:
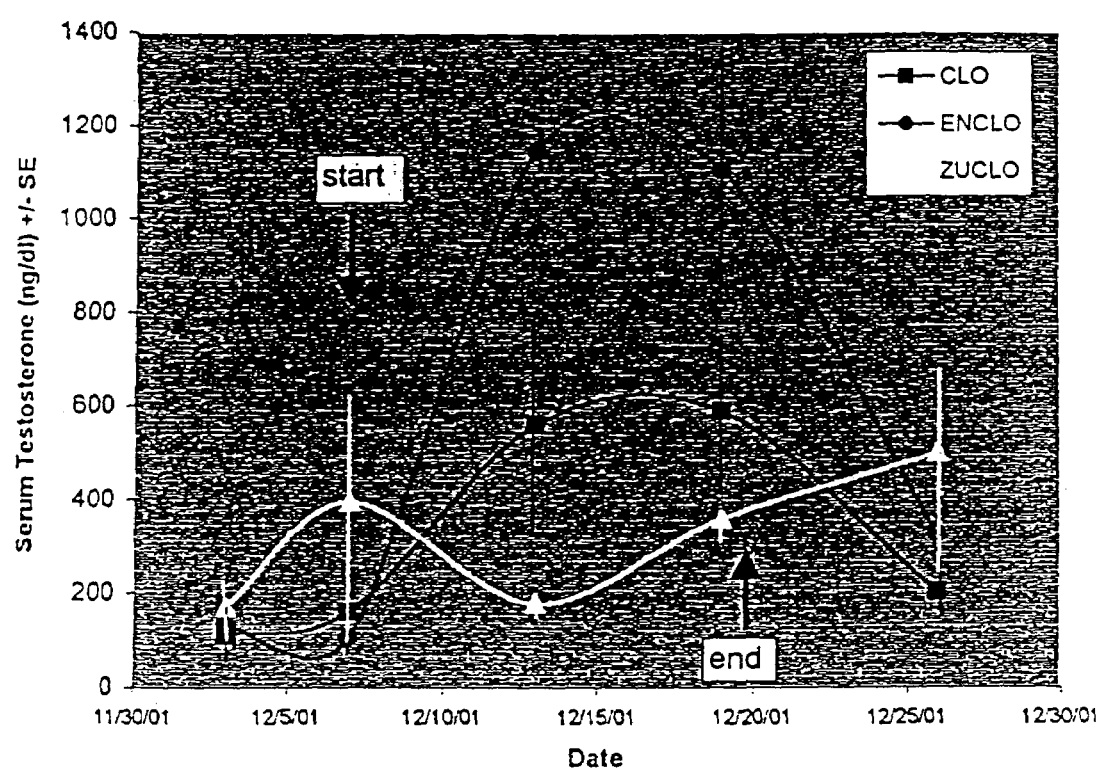
FIG. 3 is a graphic demonstration of the time course of serum testosterone levels with Clomid, Trans-clomiphene and Zuclomid.

There were significant increases in total serum testosterone in the group receiving Trans-clomiphene. See Table 1. There were no differences among groups in the baseline period or at day 0. There were also no differences among the three groups 7 days after treatment (the washout period). However, Trans-clomiphene produced higher levels of testosterone compared to Clomid and Zuclomid on day 6 ($p=0.03$ and $p=0.00002$ respectively and compared to Zuclomid on day 12 ($p=0.047$). Zuclomid clearly did not raise total serum testosterone to any extent. Compared to the animals receiving Trans-clomiphene, the animal receiving Clomid exhibited more variable total testosterone levels on day 6 and later as judged by their coefficients of variations. When we looked at the time course of the effects (FIG. 3), we determined that only Trans-clomiphene significantly and statiscally raised total serum testosterone on days 6 and 12 compared with either baseline or day 0 values. Moreover cessation of Trans-clomiphene treatment, resulted in a significant drop in the level of total serum testosterone between day 12 and day 18 (washout). This indicates that trans-clomiphene is readily cleared from the circulation consistent with the metabolic clearance seem for Trans-clomiphene in humans. Trans-clomiphene was clearly better and more consistent than Clomid itself and Zuclomid was ineffective.

2. Effects on Cholesterol Levels

Treatment with Trans-clomiphene tended to decrease serum cholesterol and Zuclomid tended to increase serum cholesterol. Preliminary analysis indicated that the changes in cholesterol levels were not statistically significant and that the changes were within the normal range. Due to the observed trend for the two isomers to demonstrate opposite effects on cholesterol levels over a short period of time, further analysis was conducted.

Detailed analysis indicated that treatment with Trans-clomiphene resulted in an 8% decrease in serum cholesterol levels. Conversely, treatment with Zuclomid resulted in a 22% increase in serum cholesterol levels. Treatment with Clomid resulted in a slight increase in serum cholesterol levels. These results indicate that Trans-clomiphene may be used for treating HIV patients who suffer from lipodystrophy accompanied by high levels of serum cholesterol. These results also indicate that Trans-clomiphene may be more benign than Zuclomid with respect to serum cholesterol if used chronically for increasing testosterone levels and maintaining muscle mass.

3. Effects on Lymphocyte Levels

All the Clomids tested had effects on the white blood cell (WBC) population, the most striking was that of Trans-clomiphene on raising the counts of lymphocytes and eosinophiles. The effects are not as straightforward as they would seem to be. There appears to be a strong effect of Enclomid on lowering the percent of granulocytes in the blood. The effects are very strong after the 7-day washout period when the values are decreased below the normal

TABLE 1

| | | \multicolumn{5}{c}{Serum Testosterone Levels (ng/dl)} | | | | |
|---|---|---|---|---|---|---|
| Group | ID | baseline Dec. 3, 2001 | 0 day Dec. 7, 2001 | 6 days Dec. 13, 2001 | 12 days Dec. 20, 2001 | wash-out Dec. 26, 2001 |
| CLO | 7500 | 79.01 | 76.15 | 940.97 | 891.5 | 150.9 |
| | 9012 | 97.55 | 305.24 | 585.92 | 555.6 | 316.3 |
| | 9097 | 158.06 | 102.94 | 151.12 | 318.9 | 143.6 |
| | mean | 111.5 | 161.4 | 559.3 | 588.7 | 203.6 |
| | SD | 41.3 | 125.2 | 395.6 | 287.7 | 97.7 |
| ENCLO | 7223 | 64.57 | 74.96 | 1223.8 | 633.6 | 307.2 |
| | 8021 | 166.86 | 133.59 | 1128.2 | 1466 | 399.2 |
| | 8369 | 170.45 | 106.47 | 1081.1 | 1166 | 271 |
| | mean | 134.0 | 105.0 | 1144.4 | 1088.5 | 325.8 |
| | SD | 60.1 | 29.3 | 72.7 | 421.6 | 66.1 |
| ZUCLO | 7438 | 124.84 | 210.4 | 137.51 | 314.5 | 359.7 |
| | 8292 | 104.66 | 67.37 | 169.98 | 406.1 | 860.5 |
| | 10098 | 282.29 | 904.82 | 227.95 | 353.0 | 274.1 |
| | mean | 170.6 | 394.2 | 178.5 | 357.9 | 498.1 |
| | SD | 97.3 | 448.0 | 45.8 | 46.0 | 316.8 |
| | ANOVA | p = 0.61 | p = 0.43 | p = 0.007 | p = 0.57 | p = 0.256 |
| | K-W | p = 0.56 | p = 0.84 | p = 0.051 | p = 0.079 | p = 0.252 |

There where no change in serum LH or FSH. The ratio of total serum testosterone to LH followed the same pattern as total serum testosterone, suggesting a lack of dependence (data not shown). There was also no change in body weight during the 12 day study. There was a decrease in serum prolactin (PRL) during the study in the group receiving Trans-clomiphene, suggesting an effect of antiestrogen that has been described in part (Ben-Jonathan and Hnasko, 2001) and expected on the basis of the fact that as men age, testosterone declines and Prolactin increase (Feldman et al., 2002).

range. (This time course could reflect the relatively long time required to affect changes in the WBC population.) There is little sexual dimorphism in baboons with respect to the white blood cell populations, so the effects are more likely to be due to the compound itself than changes in testosterone. However, when we look at the calculated count of granulocytes using the WBC count, we find no differences in granulocyte count due to any compound. Concomitantly, it is the lymphocyte story that is the most interesting. Both the count and percent lymphocytes in the population increase with Trans-clomiphene treatment. Whereas the mean values of percent lymphocytes remain in the normal range, given the trend for an increase in WBC count, the net effect is an increase in lymphocyte count with Trans-clomiphene. This eosinophil result is analogous.

4. Effects on Clinical Chemistry Parameters

The mean values for each parameter did not differ among the three groups for any test parameter at the beginning of the study as determined by ANOVA or by the Kruskal-Wallis test. All groups exhibited normal values at each parameter except for (1) serum sodium; a related calculated parameter, anionic gap, which were low for all nine baboons throughout the trial; (2) serum glucose; and (3) BUN which were high on day 0 for the group which would be treated with Trans-clomiphene. On day 12 of treatment and 7 days after treatment (washout), there were no differences among groups for any parameter except anionic gap that showed that the Clomid and Zuclomid groups had lower values than the Trans-clomiphene group. The values of serum sodium and anionic gap appear to be anomalies associated with this group of baboons.

There were substantive effects on the red blood cell population with Trans-clomiphene and Zuclomid and on hematocrit with Zuclomid. All the compounds lower the mean cell hemoglobin concentration (MCHC) either at day 0 or at the endpoint. With no change in mean cell hemoglobin (MCH) and an increase in the mean cell volume (MCV), the lowering of MCHC is predictable. Although testosterone might be expected to raise hematocrit, only Zuclomid treatment, which did not increase total serum testosterone, demonstrated a statistical difference. Clearly, men in a clinical trial that uses Zuclomid should be monitored for the characteristics of their red blood cell population. Trans-clomiphene would be predicted to have less of an effect.

There appears to be a clear effect of 12-day Trans-clomiphene treatment on platelets although the values found stayed within the normal range. One thing to consider here is the sexual dimorphism in platelet counts between male and female baboons (279 for males vs. 348 for females). This is likely to be due to hormones. Since the Trans-clomiphene group demonstrated increased testosterone, the lowering of the platelet count could be secondary to the change in testosterone in this group. Moreover, treatment with Trans-clomiphene pushed the platelet count to its normal male level from a day 0 level that was the high end of the normal range for this group. Trans-clomiphene would not necessarily predict a deleterious effect on platelets.

The increase in serum glucose with Clomid or Zuclomid was within the normal range. In the case of Trans-clomiphene where the mean serum glucose values were high on day 0, there were no increases with treatment. There was no evidence that Trans-clomiphene would have a deleterious effect on blood glucose.

No clearly adverse effects on liver function are apparent as judged by the enzymes AST and ALT. The trend in these values was a decrease with treatment. An increase in the level of enzymes in the serum would indicate liver damage. ALT/SGPT was out of range low at the end of the study for the Clomid group although the differences over the treatment period were not statistically significant. The changes with Trans-clomiphene and Zuclomid were within the normal range. AST is depressed in pregnancy; thus the action of an estrogen agonist such as Zuclomid in lowering the marginal AST level could be rationalized. Alkaline phosphatase (ALP) is also found in the liver and is elevated various disease states. The lowering of ALP argues further against hepatic damage. There were no changes in serum albumin, also a liver product. A strong suppression of serum albumin over an extended time period could contribute to free serum steroid hormone levels in humans although a more important role is played by sex hormone binding globulin. As a bottom line, none of the compounds could be linked to liver damage on the basis of the parameters assayed.

Osteoblastic activity and diseases of the bone are accompanied by high serum ALP values. ALP was not elevated following Zuclomid treatment and was decreased in value following Trans-clomiphene treatment. The trends would predict a more benign result for the use of Trans-clomiphene compared to Zuclomid.

Although BUN and BUN/creatinine were altered during the study in the Clomid and Trans-clomiphene groups, the lack of a definitive change in creatinine argues against renal dysfunction. A loss of glomerular filtration capacity would result in an increase in BUN. Decreased BUN occurs in humans due to poor nutrition (not likely in a controlled setting), or high fluid intake (presumably accompanied by edema). Also, despite an increase in total serum testosterone between day 0 and Day 12 with Trans-clomiphene, there were no differences between serum creatinine values, arguing against an increase in muscle mass over this short time interval.

Serum sodium levels were lower than reference values for all animals throughout the study. Serum carbon dioxide was higher than reference values on day 12 for the Clomid and Zuclomid groups. Serum anion gap was lower for all animals throughout the study, paralleling the sodium results. Trans-clomiphene raised this parameter towards normal values. Throughout all treatment periods, the detected electrolyte imbalances remain elusive but might be part of the same fluid derangement phenomenon suggested by the BUN results.

The foregoing results indicate that Trans-clomiphene is more effective than Clomid or Zuclomid at enhancing total serum testosterone. Zuclomid is clearly not effective and that deficiency limits any use of Clomid for hypogonadism, particularly since the Zuclomid component of Clomid would predominate in the circulation over time given its longer half-life.

EXAMPLE 2

Treating Wasting in HIV-Infected Individuals

Prior to administration of trans-clomiphene, blood samples are taken from subjects individuals and testosterone levels are measured using methodologies described for example in Matsumoto, et al. Clin. Endocrinol. Metab. 56; 720 (1983) (incorporated herein by reference). Sex hormone binding globulin (SHBG), both free and bound to testosterone, may also be measured as described for example in Tenover et al. J. Clin. Endocrinol. Metab. 65:1118 (1987) which describe measurement of SHBG by both a [$^3$H] dihydrotestosterone saturation analysis and by radioimmunoassay. Non-SHBG-bound testosterone levels (bioavailable testosterone) are also measured for example according to Tenover et al. J. Clin. Endocrinol and Metab. 65:1118 (1987). See also Soderguard et al. J. Steroid Biochem 16:801 (1982) incorporated herein by reference.

Patients are given daily dosages of 1.5 mg/kg clomiphene, wherein the ratio of trans-clomiphene to cis-clomiphene is greater than 71/29. Patients are monitored for testosterone levels and increases in muscle mass such that the dosage amount and dosage frequency may be adjusted to achieve therapeutic levels of testosterone and improvements in muscle mass in the patient.

EXAMPLE 3

Treating Lipodystrophy in HIV-Infected Individuals

Prior to administration of trans-clomiphene, blood samples are taken from subject individuals and cholesterol levels are measured using methodologies described for example in Cooper, et al. (Selected methods for the small clinical chemistry laboratory. W. R. Faulkner and S. Meites, eds. Am. Assoc. for Clin. Chem., Washington, D.C. Pages 165–174), which is incorporated herein by reference.

Patients are given daily dosages of 1.5 mg/kg clomiphene, wherein the ratio of trans-clomiphene to cis-clomiphene is greater than 71/29. Patients are monitored for cholesterol levels and decrease in symptoms associated lipodystrophy such that the dosage amount and dosage frequency may be adjusted to achieve therapeutic levels of cholesterol and improvements in symptoms associated lipodystrophy in the patient.

We claim:

1. A method for treating symptom of wasting in a human infected with human immunodeficiency (HIV), comprising administering to the human a composition comprising cis-clomiphene and trans-clomiphene or pharmaceutically acceptable salts thereof and optionally one or more pharmaceutically acceptable diluents, adjuvants, carriers or excipients in an effective amount to treat said symptom of wasting in the human infected with HIV, wherein the weight (w/w) ratio of trans-clomiphene to cis-clomiphene is greater than 71/29.

2. The method of claim 1 wherein the composition consists essentially of trans-clomiphene or a pharmaceutically effective salt thereof and optionally one or more pharmaceutically acceptable diluents, adjuvants, carriers or excipients, in an effective amount to treat said symptom of wasting in the human infected with HIV.

3. The method of claim 2, wherein the trans-clomiphene is in a dosage range of 1–200 mg per day.

4. The method of claim 3, wherein the trans-clomiphene is in a dosage range of 50 mg per day.

5. The method of claim 2, wherein the trans-clomiphene is administered in a dosage of 1.5 mg/kg per day.

6. The method of claim 2, wherein the composition consists essentially of 12.5 mg of trans-clomiphene or a pharmaceutically effective salt thereof.

7. The method of claim 1, wherein the composition is a capsule.

* * * * *